United States Patent [19]
Yasohama et al.

[11] Patent Number: 5,548,214
[45] Date of Patent: * Aug. 20, 1996

[54] ELECTROMAGNETIC INDUCTION INSPECTION APPARATUS AND METHOD EMPLOYING FREQUENCY SWEEP OF EXCITATION CURRENT

[75] Inventors: Kazuhiko Yasohama, Koganei; Hiroaki Kohama, Tokyo, both of Japan

[73] Assignee: Kaisei Engineer Co., Ltd., Tokyo, Japan

[ * ] Notice: The portion of the term of this patent subsequent to May 14, 2013, has been disclaimed.

[21] Appl. No.: 980,562

[22] Filed: Nov. 23, 1992

[30] Foreign Application Priority Data

Nov. 21, 1991  [JP]  Japan ................................... 3-306296
Nov. 29, 1991  [JP]  Japan ................................... 3-316969

[51] Int. Cl.$^6$ ............................................. G01N 27/82
[52] U.S. Cl. ................................... 324/240; 324/228
[58] Field of Search ........................ 324/207.16, 207.17, 324/228–243, 260, 217

[56] References Cited

U.S. PATENT DOCUMENTS

| | | | |
|---|---|---|---|
| 3,576,489 | 4/1971 | Law ................................... | 324/233 |
| 3,686,564 | 8/1972 | Mallick, Jr. et al. ................ | 324/243 |
| 4,079,312 | 3/1978 | Osborn et al. ...................... | 324/226 |
| 4,563,644 | 1/1986 | Lenander et al. ................... | 324/232 |
| 4,563,645 | 1/1986 | Kerr ................................... | 324/329 |
| 4,818,936 | 4/1989 | Kemlo ................................. | 324/232 |
| 5,017,869 | 5/1991 | Oliver ................................. | 324/232 |

FOREIGN PATENT DOCUMENTS

| | | |
|---|---|---|
| 0146091 | 6/1985 | European Pat. Off. . |
| 61-066958 | 4/1986 | Japan . |
| 2109112 | 5/1983 | United Kingdom . |

*Primary Examiner*—Sandra L. O'Shea
*Assistant Examiner*—J. M. Patidar
*Attorney, Agent, or Firm*—Wenderoth, Lind & Ponack

[57] ABSTRACT

An electromotive induction current which is detected by an induction coil placed in an electromagnetic field generated by applying an alternating current to an exciting coil distinctively changes with the frequency of the applied alternating current in accordance with the conditions of an object placed in the electromagnetic field. By analyzing the change in amplitude and/or frequency phase of the electromotive induction current, the physical properties, size and relative position of the object and internal defects such as a crack and pin hole in the object can be measured precisely.

11 Claims, 8 Drawing Sheets

ELECTROMAGNETIC INDUCTION INSPECTION APPARATUS AND METHOD EMPLOYING FREQUENCY SWEEP OF EXCITATION CURRENT

BACKGROUND OF THE INVENTION

1. Field of the Invention

This invention relates to an inspection device and method for detecting the existence of an object to be inspected or an abnormality in the object by use of electromagnetic induction, and more particularly, to an inspection device and method for precisely inspecting the conditions such as internal defects of the objects of various materials using a change in amplitude and/or phase of an electromotive induction current induced electromagnetically by an induction coil placed in an electromagnetic field.

2. Description of the Prior Art

Magnetic flux changes with the existence of an object in an electromagnetic field generated with application of an alternating current, thereby changing the inductance of a coil placed in the electromagnetic field. The inductance of the coil changes proportionally with the dielectric constant, magnetic permeability, size, relative position and other possible inductive factors of the object placed in the electromagnetic field. When some of the inductive factors of the object located in the electromagnetic field are known, the other unknown factors can be calculated from the detected change of the inductance.

A variety of non-destructive inspection devices using such principles of electromagnetic induction are known for recognition of the existence or identification of given objects.

Figure 1:
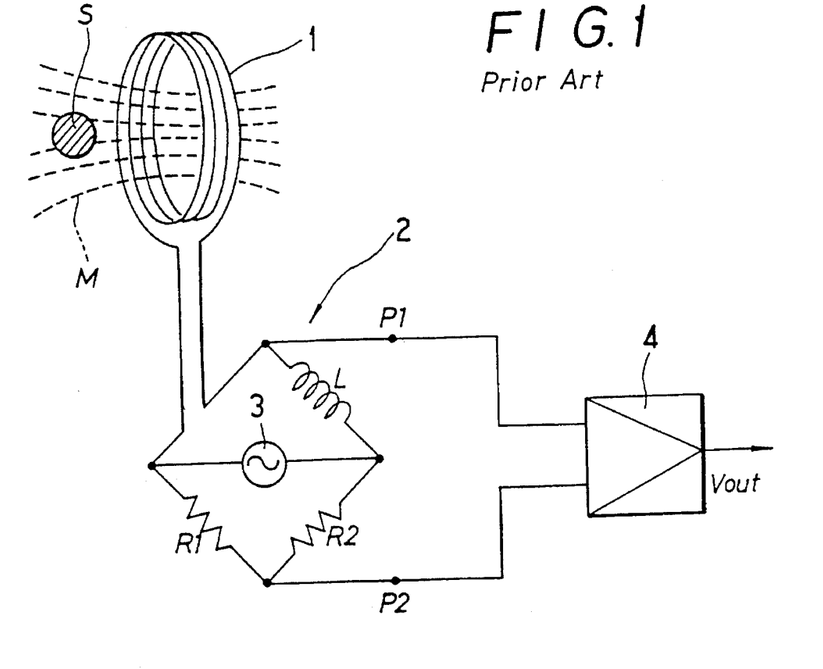
FIG. 1 is a schematic view showing a conventional self-induction type inspection device.

One of the typically known inspection devices of this type is shown in FIG. 1. This inspection device comprises an electromagnetic coil 1 (self-induction coil) which generates an electromagnetic field with an alternating current and is provided in one arm of a bridge circuit 2. In the bridge circuit, a pair of resistors R1 and R2 are equal in impedance to each other. When the coil 1 is excited in the normal state in which no substance exists in the electromagnetic field induced by applying an alternating current from a power source 3 to the coil 1, the inductance of the coil 1 is equal to an adjacent inductor L, and therefore, the bridge circuit 2 on the whole is in equilibrium. In this steadily balanced state, a measuring instrument 4 (usually a galvanometer or sensitive micro-ammeter) connected to diagonal output points P1 and P2 of the bridge circuit 2 generates no output (Vout=0).

However, when an object S to be inspected is placed in the elecltromagnetic field M induced by the coil 1, the self-inductance of the coil 1 changes with the coefficient of induction of the object S, thereby breaking the equilibrium state of the bridge circuit, resulting in a non-equilibrium output voltage Vout across the output points P1 and P2. Generally, the non-equilibrium output from the bridge circuit is amplified by a differential amplifier 4.

By analyzing the change of the output voltage Vout, not only the physical properties and size of the object but also the speed at which the object moves in the magnetic field can be determined. In this case, the bridge circuit is formed in the equilibrium state when a reference body is placed in the magnetic field generated by the inductor L and a normal object is placed near the coil 1.

The aforementioned inspection device is commonly called the "self-induction type" inspection device.

Figure 2:
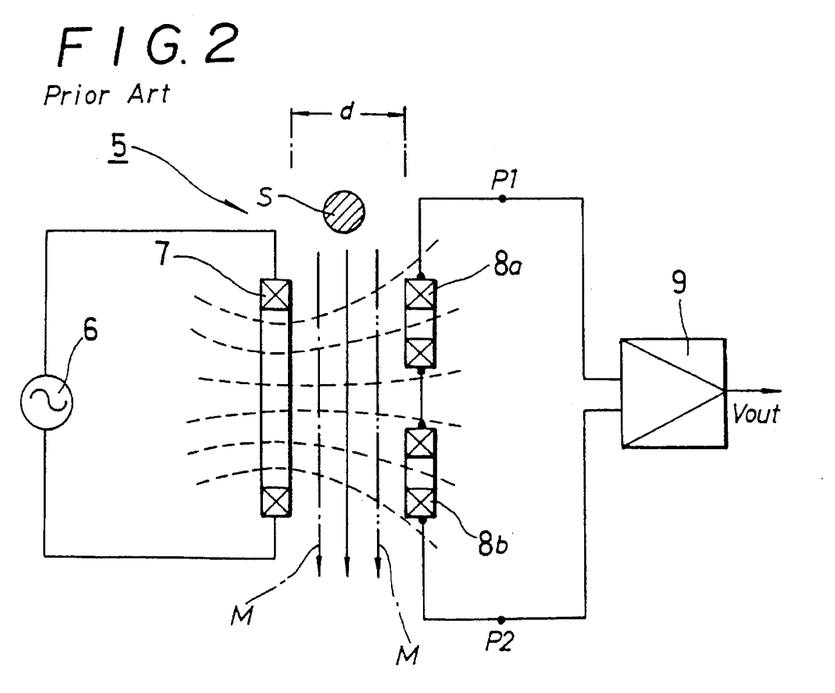
FIG. 2 is a schematic view showing a conventional mutual-induction type inspection device.

Another type of known inspection device uses mutual induction as shown in FIG. 2. This inspection device 5 comprises an exciting coil 7 (primary coil) excited by a power source 6 to generate an electromagnetic field M and a pair of induction coils 8a and 8b (secondary coil) which acquires the electromagnetic field (magnetic flux) generated by the exciting coil 7 and inducing an electromotive current, and a differential amplifier 9. The induction coils 8a and 8b are wound in opposite directions to each other and are differentially connected in series, so that the electromotive currents induced in the respective induction coils 8a and 8b by the electromagnetic field from the exciting coil 7 cancel each other in the normal equilibrium state. That is to say, in the equilibrium state of the induction coils 8a and 8b, the differential voltage across the output points P1 and P2 becomes zero, i.e. Vout=0.

In general, the mutual induction type inspection device has an inspection path (space d) between the exciting coil 7 and paired induction coils 8a and 8b for allowing a given object S to pass therethrough across the magnetic flux M of the magnetic field generated by exciting coil 7. When passing the object S through the inspection path across the magnetic flux induced by the exciting coil 7, the magnetic flux which reaches the induction coils 8a and 8b undergoes a change in interlinkage. Namely, the paired induction coils 8a and 8b respectively acquire different interlinkage numbers of the magnetic flux, to thereby break the balanced state of the induction coils 8a and 8b (nonequilibrium state), As a result, a differential voltage Vout is generated from the differential amplifier 9 . Thus, it is possible to recognize the physical properties and size of the object S or to detect defects such as a crack and pin hole in the object S.

In the prior art inspection devices noted above, since the nonequilibrium state in electromagnetic induction is determined using the differential voltage derived from the bridge circuit 2 or the series connected induction coils 8a and 8b, the change in induced electromotive current which is caused by passing the object across the magnetic flux must be measured with a notably high accuracy in order to increase the measurement accuracy.

In the self-induction inspection device illustrated in FIG. 1, however, because the rate of change in self-induction (difference between the base inductance and the inductance undergoing a change) is very small, it has been substantially impossible or difficult to precisely detect such a small change in inductance. Thus, the conventional inspection device of the self-induction type has a low sensitivity and cannot be applied to inspect a given object having a low rate of change in inductance and nonmetallic objects such as synthetic resin.

On the other hand, the mutual induction inspection device of FIG. 2 has the inspection path defined between the exciting coil 7 (primary coil) and paired induction coils 8a and 8b (secondary coil). The induction efficiency is in inverse proportion to the dimension of the inspection path (space d between the exciting coil and the paired induction coils). This device is disadvantageous in that the inspection path is limited in dimension from the standpoint of performance and adds to the total system size and prevents a large object to be inspected from passing therethrough.

Even if the inspection path is made wide for permitting such a large object to pass therethrough, the inspection accuracy is decreased proportionally and a slight change in induction cannot be detected.

Moreover, the inspection device of the mutual induction type inevitably has a fatal disadvantage in that, when the object S approaches one of the paired induction coils (coil 8*a* in FIG. 2), not only the coil 8*a* but also the coil 8*b* is affected by the object S to cause the coil 8*b* to change the inductance of the coil 8*b*. Though either of the induction coils should have, as a reference inductor, a fixed inductance relative to the other coil close to the object S, both the coils change in inductance even when the object S approaches one of the induction coils. Namely, the induction of the induction coil remote from the object S changes in a complicated manner with the relative position of the object S to the induction coils. Therefore, a change in inductance of one of the induction coils cannot be determined precisely, resulting in a conspicuous decrease in measuring accuracy.

As noted above, the conventional inspection devices using electromagnetic induction are restricted in the size of the object to be inspected and inevitably lead to noticeable measurement errors. Though the inspection device of this type may use an exciting current having adequate frequency with which electromagnetic induction changes markedly to increase the detecting sensitivity, it has a common disadvantage of being so limited in their range of applications as to be of no practical utility. Further, the conventional inspection device suffers a serious disadvantage such that occasionally, a change of the electromagnetic induction, which is caused by a defect in an object, is not noticeably different from that by a nondefective object. Under such circumstances, the defective object would be Judged to be good in error. Such inexpediency is possibly brought about even when the measuring sensitivity is increased. For example, when a weld portion (nugget) formed by spot welding in a metallic object is subjected to a non-destructive inspection using a change of electromagnetic induction, the electromagnetic induction detected from a normal nondefective object by the conventional inspection device using electromagnetic induction is not always fixed.

Also, not infrequently there are times when the defects such as a crack and incomplete fusion in the weld portion can hardly be detected in the form of a change of inductance according to the locations of the defects even if they are sufficient for being detected practically. In this case, disadvantageously, the defective object is possibly taken for a nondefective object.

OBJECT OF THE INVENTION

This invention is made to eliminate the drawbacks suffered by the conventional inspection devices as described above and has an object to provide an inspection device and method using electromagnetic induction, capable of precisely inspecting all sorts of objects of not only a magnetic or dielectric substance but also a nonmagnetic substance to detect a defect or abnormality in the object and further recognize the size and location of the defect with a notably high accuracy and sensitivity.

Another object of this invention is to provide an inspection device using electromagnetic induction, which is portable and easy to handle and has an excellent performance.

SUMMARY OF THE INVENTION

To attain the objects described above according to this invention, there is provided an inspection device using electromagnetic induction, comprising a power source unit for issuing an alternating current, an inspection coil unit including an exciting coil for generating an electromagnetic field with application of the alternating current from the power source unit and an induction coil for inducing an electromotive current in the electromagnetic field generated by the exciting coil, and a measuring unit for measuring a change of the electromotive current induced by the induction coil in relation to the frequency of the alternating current given from the power source unit to the exciting coil.

An inspection method using electromagnetic induction according to this invention comprises applying an alternating current having adjustable frequency to an exciting coil to generate an electromagnetic field, detecting an electromotive current induced by an induction coil placed in the electromagnetic field generated by the exciting coil, determining a reference induction change characteristic by placing a reference body in the electromagnetic field while changing the frequency of the alternating current applied to the exciting coil, detecting continuously the electromotive current induced when an object to be inspected is placed in the electromagnetic field while changing the frequency of the alternating current applied to the exciting coil, and comparing; the electromotive current affected by the object with the reference induction change characteristic.

In observing the change of the electromotive current derived from the induction coil to the exciting coil, the amplitude strength (voltage) or frequency phase of the electromotive current is measured and compared with the reference induction change characteristic determined by a preliminary test.

The induction characteristic of the induction coil changes with the change of the frequency characteristic of the alternating current applied to the exciting coil. When an object is placed in the electromagnetic field generated by the exciting coil, the electromotive current induced by the induction coil changes distinctively. The electromotive current obtained when the object exists in he electromagnetic field is compared with that obtained when no object exits in the electromagnetic field. Thus, by analyzing the change of the electromotive current relative to the reference induction change characteristic, an abnormality of the object can be detected precisely. Since the induction change characteristic is obtained by measuring electromotive current over a wide frequency range of the alternating current applied to the exciting coil, the difference between the object to be inspected and the reference body are conspicuously shown in some distinctive frequency points in the frequency range. Therefore, the comparison of the induction change characteristic of the object to be inspected with the reference induction change characteristic is effected with ease.

The pattern of the induction change characteristic of the electromotive induction current induced by the induction coil over the frequency range is distinctively shown according to not only the physical properties and size of the object but also the conditions of the relative locations and size of the defects in the object and other possible abnormalities. Thus, the various information of the object can be recognized with a high accuracy.

Since the inspection coil unit used in this invention is formed by integrating the exciting coil and the induction coil, the measuring sensitivity thereof can be increased and little affected by disturbances causing electromagnetic compatibility or the like. Also, since the exciting coil and the induction coil are united coaxially, the inductance change rate can be increased thereby improving the measuring sensitivity of the inspection coil unit.

Other and further objects of this invention will become obvious upon an understanding of the illustrative embodiments about to be described or will be indicated in the appended claims, and various advantages not referred to herein will occur to one skilled in the art upon employment of the invention in practice.

DESCRIPTION OF THE PREFERRED EMBODIMENTS

The present invention will become more fully understood from the detailed description given hereinbelow and the accompanying drawings which are given by way of illustration only, and thus are not limitative of this invention.

Figure 3:
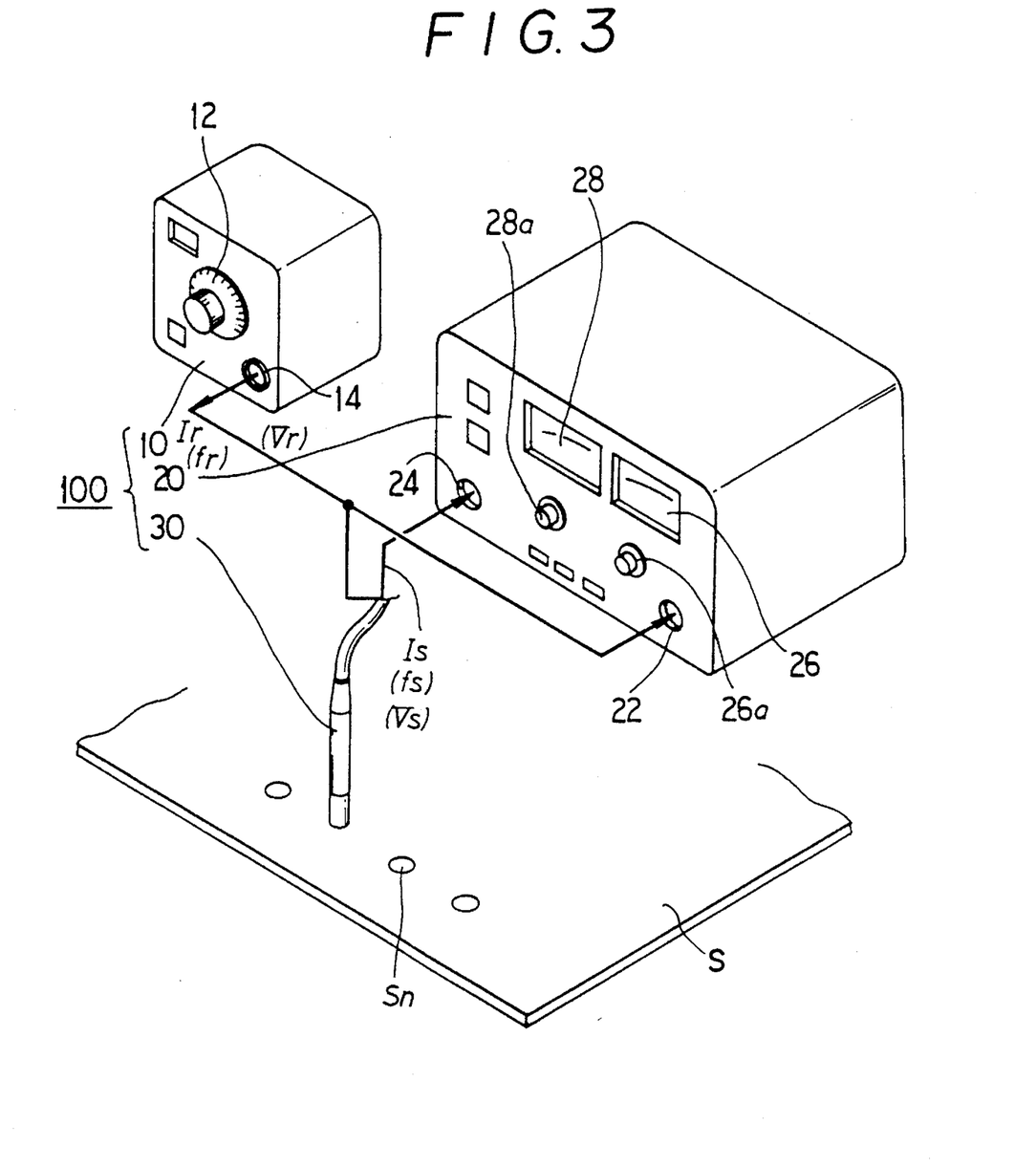
FIG. 3 is a schematic view showing one embodiment of an inspection device using electromagnetic induction according to this invention.

FIG. 3 illustrates schematically one embodiment of the inspection device using electromagnetic induction according to the present invention. This inspection device 100 includes a power source unit 10 which issues an alternating current Ir, a measuring unit 20, and an inspection coil unit 30.

The power source unit 10 has a function capable of adjusting the frequency of the alternating current Ir issued therefrom and automatically changing continuously the frequency of the current over a predetermined frequency range. The power source unit 10 has an adjusting dial 12 for manually changing the frequency of the alternating current outputted therefrom.

The measuring unit 20 in this embodiment has a function of measuring the amplitude intensity (voltage) of an input electric current. The illustrated measuring unit 20 has a reference signal input connector 22 for receiving the alternating current Ir issued from the power source unit 10 as a reference signal, an inspection signal input connector 24 for receiving an inspection signal Is, a first indicator 26 for indicating the deviation of the phase of the measured frequency fs of the signal Is relative to the reference frequency fr of the signal Ir, and a second indicator 28 for indicating the amplitude intensity of the input signal. The zero adjustment and fine adjustment of first and second indicators 26 and 28 can be effected by operating adjusting dials 26a and 28a, respectively.

Figure 4:
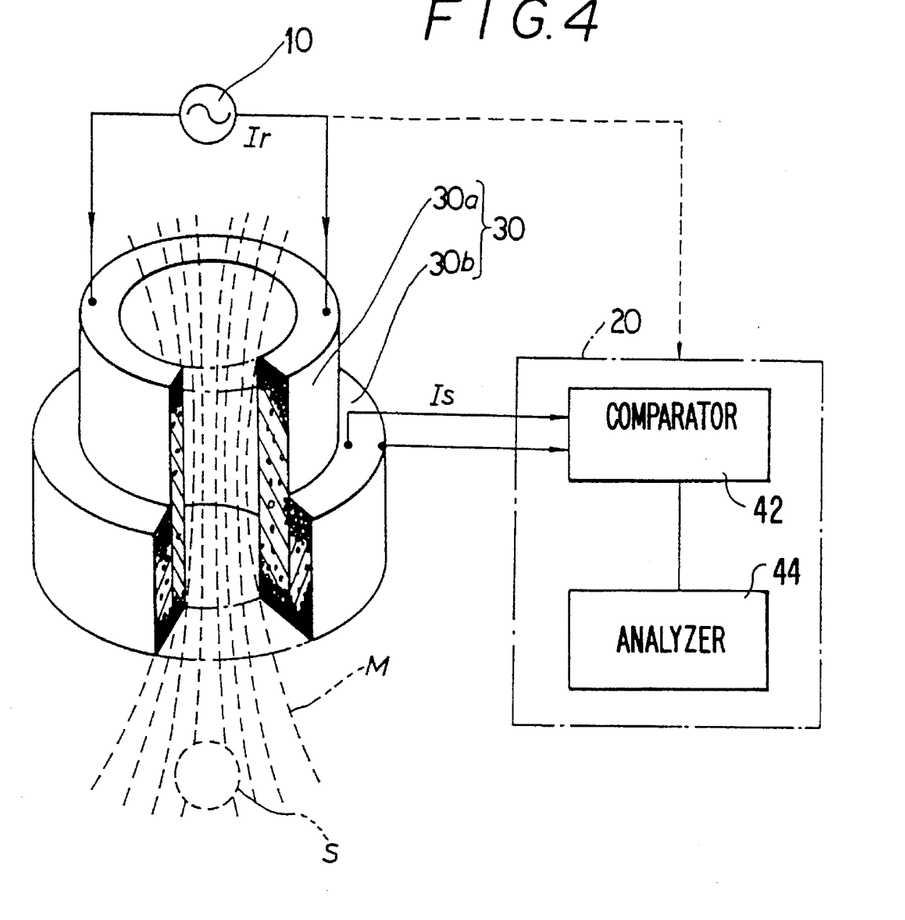
FIG. 4 is a schematic perspective view, partially in section, showing an inspection coil unit used in the inspection device of this invention.

The inspection coil unit 30 is connected to the output connector 14 of the power source unit 10 and to the input connector 24 of the measuring unit 20. As schematically shown in FIG. 4, the inspection coil unit 30 comprises an exciting coil 30a which generates an electromagnetic field M with application of the alternating current Ir from the power source unit 10, and an induction coil 30b which placed in the electromagnetic field M generated by the exciting coil 30a thereby inducing an electromotive current Is.

The exciting coil 30a serving as a primary coil and induction coil 30b serving as a secondary coil are integrally united. That is, the induction coil 30b is wound closely around at least one part of the outer periphery of the exciting coil 30a, so that the magnetic field M generated in the cylindrical hollow of the exciting coil 30a passes coaxially through the inner hollow of the induction coil 30b. Thus, the magnetic flux induced by the exciting coil 30a is all interlinked with the induction coil 30b, thereby bring about mutual inductance to induce a large electromotive current in the induction coil 30b with a notably high efficiency.

Figure 5:
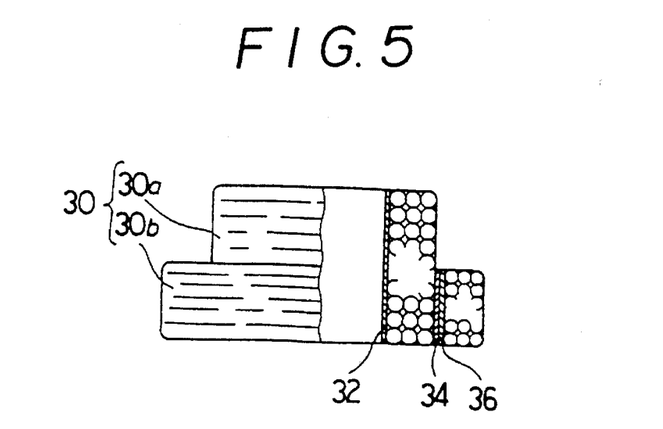
FIG. 5 is a schematic side section of the inspection coil unit of this invention.

As shown in FIG. 5, the inspection coil unit 30 is generally made by first winding a conductive wire on a bobbin 32 to form the exciting coil 30a shaped in the form of a cylinder, wrapping an electromagnetic shielding layer 34 and an insulating sheet 36 around a part of the outer periphery of the exciting coil 30a, and further winding a conductive wire around the insulating sheet 36 to form the induction coil 30b.

The bobbin 32 may be removed in putting the inspection coil unit 30 to use. This method of forming the inspection coil and the components and arrangement of the exciting coil and induction coil should not be understood as limitative.

The electromotive current induced by the induction coil 30b can be amplified so as to be processed easily by, for example, inserting the inspection coil unit 30 into a bridge circuit or the like to constitute a differential amplifier.

When the object S to be inspected is placed in the magnetic field M generated by the exciting coil 30a as shown in FIG. 4, the inductance of the induction coil 30b changes. The change of the inductance depends on various factors such as the size and physical properties of the object S. Therefore, by analyzing the change of the inductance of the induction coil 30b, the conditions of the object S can be recognized with ease.

In FIG. 3, a thin steel plate is shown as the object S by way of example. The inspection device of this invention can be applied practically to a flaw detection of a weld portion (nugget) Sn of the steel plate.

The aforementioned measuring unit 20 includes a comparator 42 and an analyzer 44. In the comparator 42, the amplitude (voltage Vs) of the current Is derived from the induction coil 30b when inspecting a given object S is compared with the reference current Ir (reference voltage Vr) which is based on the inductance of the induction coil 30b under the steady state in which nothing exists in the magnetic field generated by the exciting coil 30a. The analyzer 44 has a function of analyzing the results obtained from the comparator 42 upon comparison of the measured value with the reference value to recognize the conditions of the object S.

Figure 6:
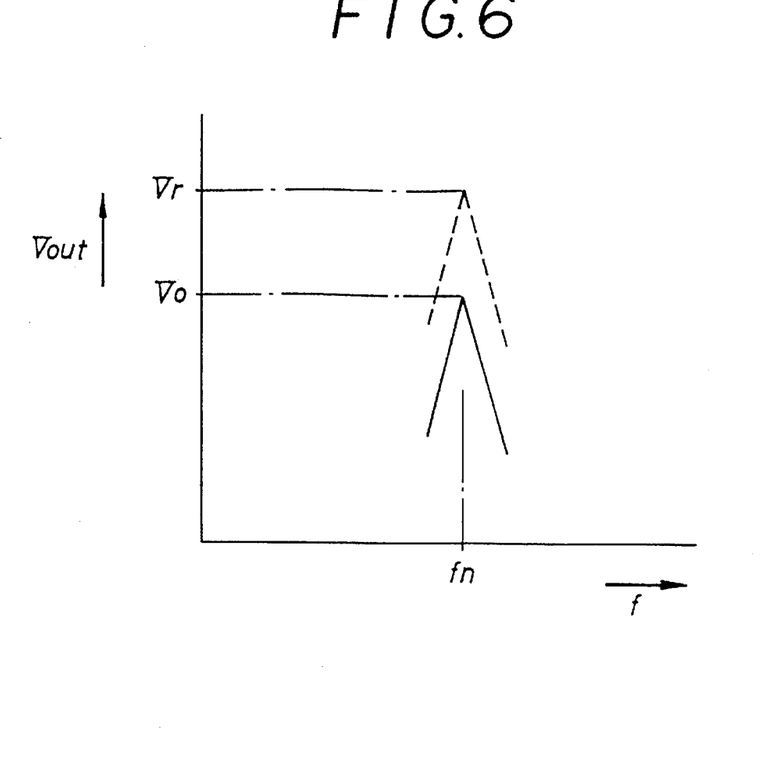
FIG. 6 is an induction characteristic diagram of the inspection coil unit of this invention.

The electromotive current from the inspection coil unit 30 has significant specific induction characteristics relative to the change of the frequency applied to the exciting coil. The induction characteristics change distinctively with the material, physical properties, relative position and size of the object S which determine the magnetic permeability of the object, existence of an alien substance in the object, and other possible heterogeneous factors. That is to say, when the object S is placed in the magnetic field generated by the exciting coil 30a, the output voltage Vout derived from the induction coil 30b changes from the voltage Vo obtained under the steady state to the voltage Vr, as shown conceptually in FIG. 6. The change rate Vr/Vo depends on the frequency fn of the current applied to the exciting coil 30a. By utilizing such variation characteristics of the induced voltage relative to the frequency, the physical properties and structural conditions of the object S can be recognized with a high accuracy.

The experiment actually conducted using the inspection coil unit of this invention revealed that the electromotive induction current induced by the induction coil definitely varies with the change of the frequency of the alternating current applied to the exciting coil.

Figure 7:
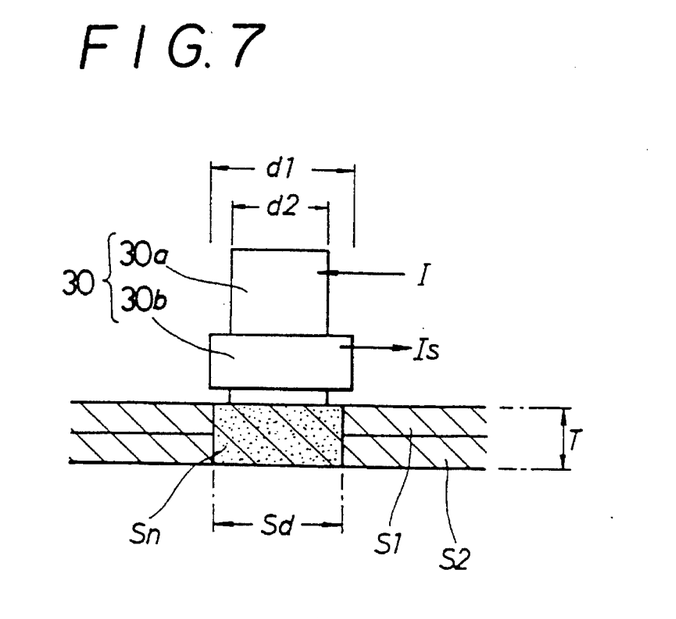
FIG. 7 is a schematic side view showing the state of inspecting a weld portion with the inspection device of this invention.

When the experiment was carried out, specimen objects were prepared by joining two steel plates S1 and S2 (made of SPCC) together and-spot-welding the joined plates to form welding portions (nuggets) Sn, as shown in FIG. 7. In the experiment, there was investigated how a voltage of the induction current changes with the frequency of an alternating current (I) applied to the exciting coil. The inspection coil unit 30 used in this experiment comprises the primary exciting coil 30a having an outer diameter (2) of 3 mm, which is made by winding of 300 turns of conductive wire of 0.1 mm in diameter, and the secondary induction coil 30b having an outer diameter (1) of 8 mm, which is made by a winding of 300 turns of conductive wire of 0.1 mm in diameter. To exciting coil 30a, an alternating current (I) of 100 mA and 6 volts was applied. The thickness (T) of the joined plates was 2.5 mm, and the diameter (Sd) of the welding portion (nugget) was less than 8 mm.

In the experiment, the induction currents (Vout) obtained by attaching the inspection coil unit to the nondefective nuggets (GD) and the defective nuggets were measured while continuously changing the frequency (f) of the alternating current (I) from about 0.7 kHz to about 95 kHz.

Figure 8:
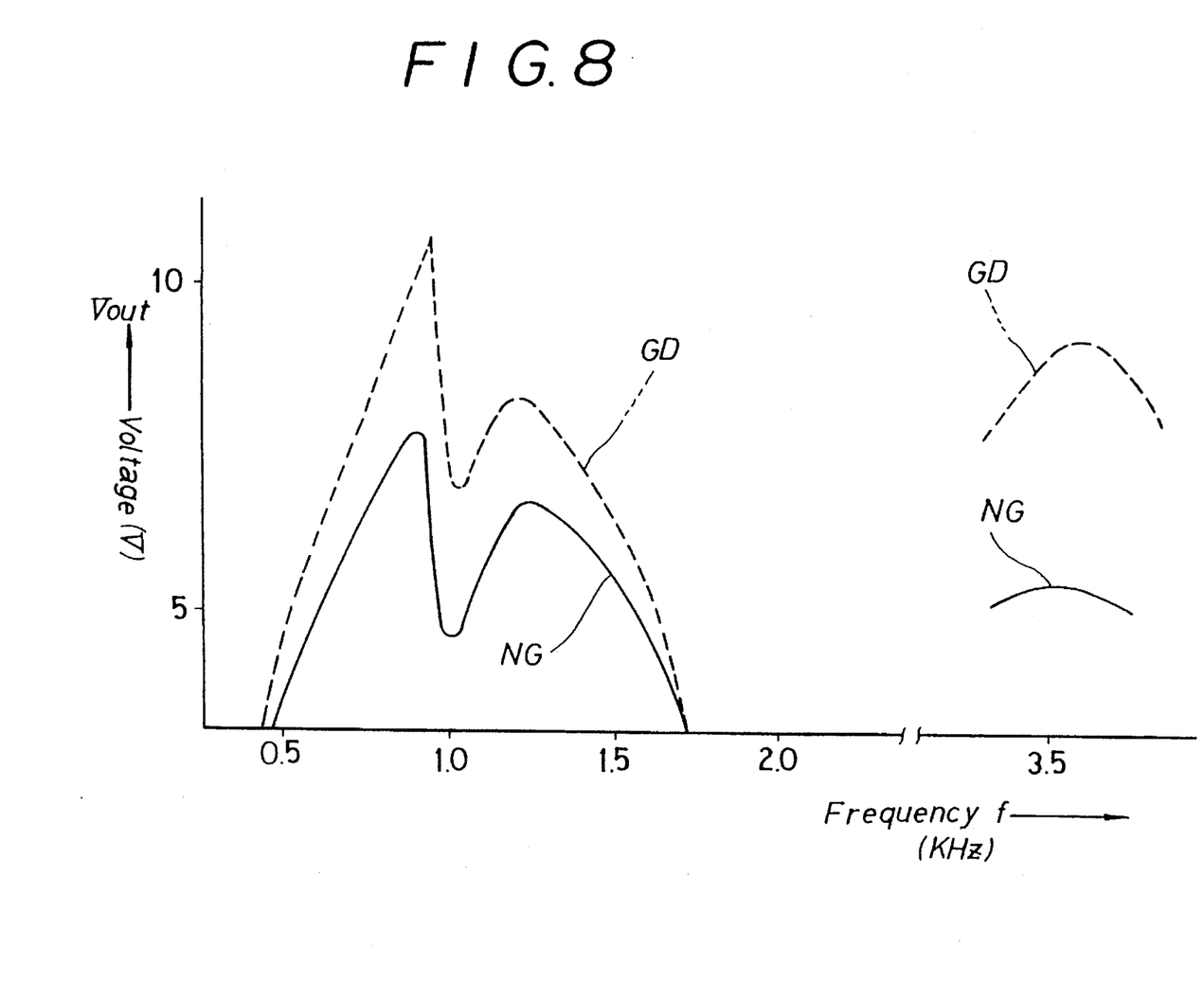
FIG. 8 is a frequency-induction characteristic diagram of the inspection coil unit of this invention.

FIG. 8 is a frequency-voltage characteristic graph showing the results of the experiment. As is evident from the characteristic graph, the induction outputs (voltage) obtained from the nondefective nuggets (GD) and defective nuggets (NG) distinctively change continuously over the whole frequency range from a low frequency to a high frequency. Particularly, the conspicuous difference in induction output appeared clearly in the range from a middle frequency of 0.7 kHz to a high frequency of 37 kHz.

Figure 13:
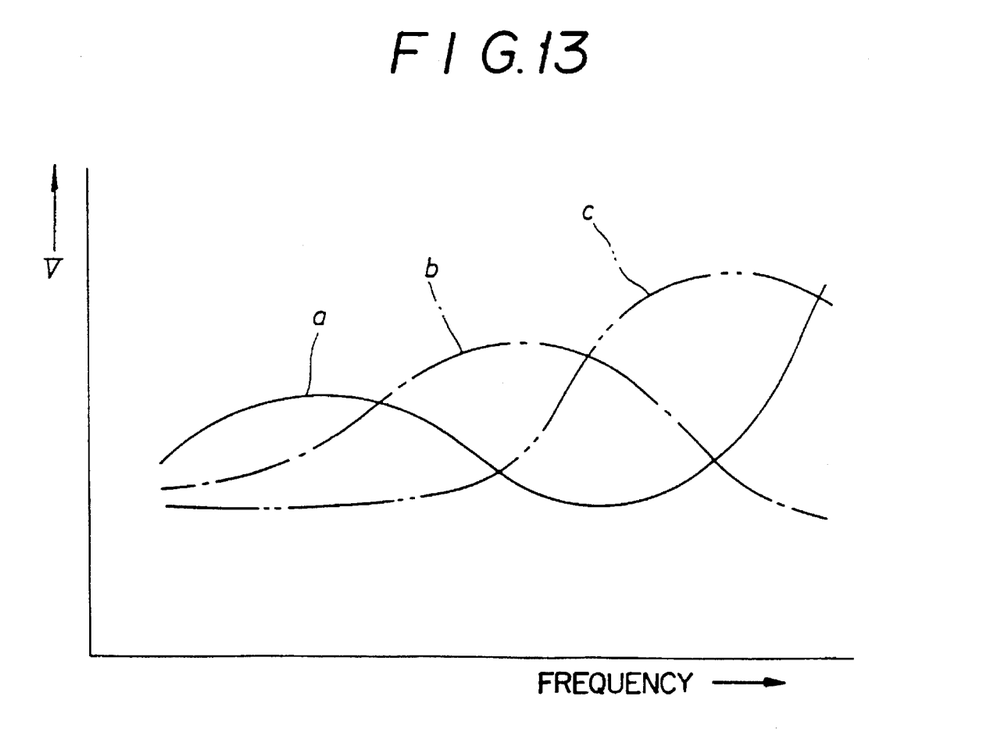
FIG. 13 is a frequency-induction characteristic diagram showing the characteristic curves varying with the defects in the objects to be inspected.

In addition, the frequency-voltage characteristics as described above show different induction patterns in accordance with the structural conditions of the objects (specimens). To be more specific, the characteristic pattern of the induction voltage generated by the induction coil 30a relative to the frequency of the alternating current applied to the exciting coil 30b distinctively changes according to the existence and conditions of defects such as a crack, pin hole and incomplete fusion in the weld portion (nugget). When the nuggets Sn formed by spot-welding have internal defects d1–d5 as schematically illustrated in FIG. 9 to FIG. 12, the different frequency-voltage characteristic patterns are obtained. For example, characteristic patterns will change with differing defects as shown by the curves a, b and c illustrated in the frequency-voltage diagram of FIG. 13.

Figure 9:
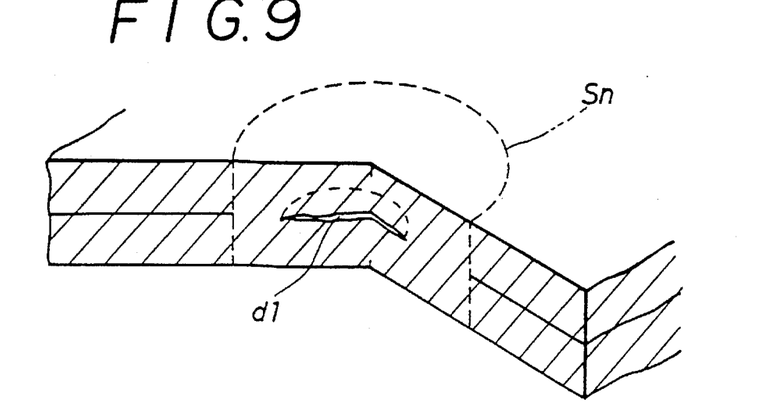
FIG. 9 is a perspective section showing a first object to be inspected.
Figure 10:
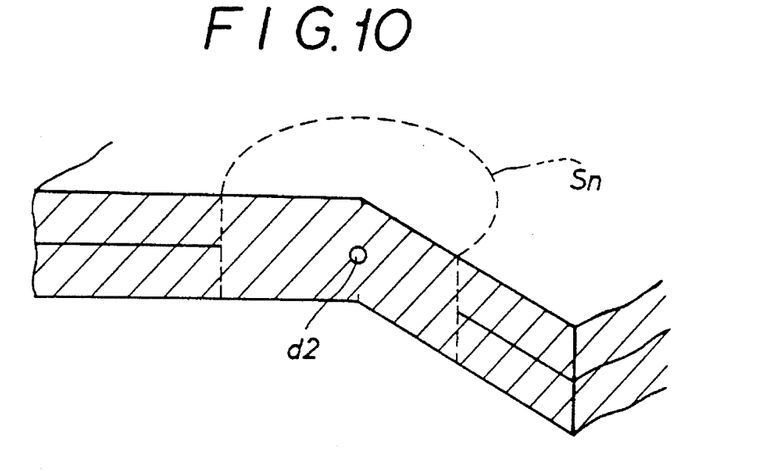
FIG. 10 is a perspective section showing a second object to be inspected.
Figure 11:
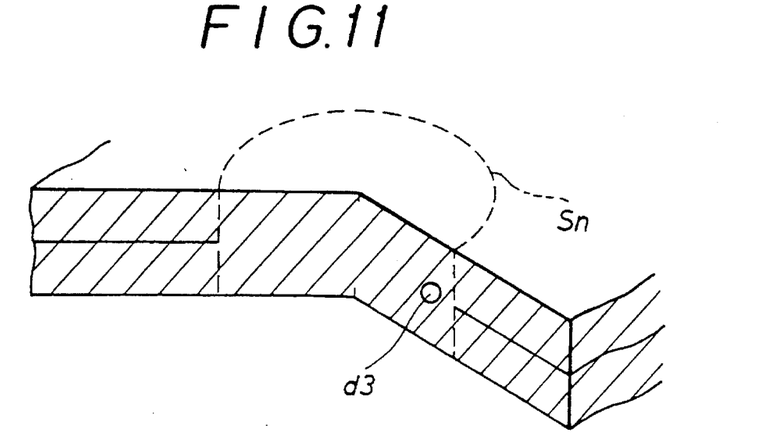
FIG. 11 is a perspective section showing a third object to be inspected.
Figure 12:
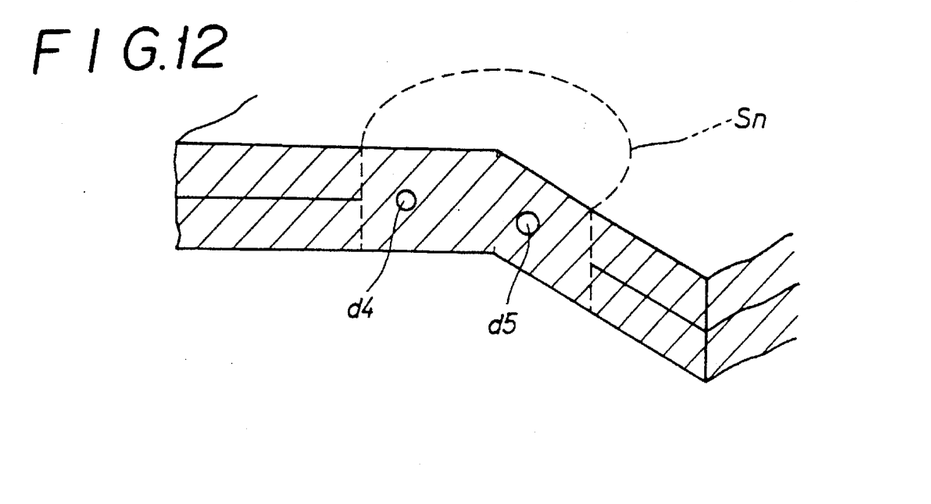
FIG. 12 is a perspective section showing a fourth object to be inspected.

The defect d1 of the nugget Sn of FIG. 9 is a crack. The defect d2 in FIG. 10 is a pin hole formed in the central portion of the nugget Sn. The defect d3 in FIG. 11 is a pin hole formed in the peripheral portion of the nuggets Sn. The nugget Sn of FIG. 12 has two pin hole defects d4 and d5. By analyzing the frequency-voltage characteristics obtained by measuring the induction voltages in respect of these defective nuggets, the relative location, shape and size of the defects in the nuggets can be clearly discriminated.

Though the weld portions are used as the objects to be inspected with the inspection device of this invention in the aforementioned embodiment, of course, this should not be understood as limitative. That is, the kind and configuration of the object to be inspected are by no means limited and any other objects may be dealt with regardless of the material, size, physical properties and structure of the object by preparing frequency-voltage data corresponding to various objects.

As is apparent from the foregoing, all sorts of the objects of not only a magnetic or dielectric substance but also a nonmagnetic substance can be inspected to detect a defect or abnormality in the object and further recognize the size and relative location of the defect with a notably high accuracy and sensitivity.

In a second embodiment of this invention, the object is inspected using a change of the frequency phase of the induction current derived from the induction coil 30b.

The frequency phase of the induction current induced electromagnetically by the induction coil 30b changes distinctively according to the existence of the object in the electromagnetic field generated by the exciting coil 30a. Thus, by comparing the phase of the frequency fs of the electromotive induction current Is derived from the induction coil 30b with that of the frequency fr of the alternating current Ir given from the power source unit 10 to the exciting coil 30a, the existence and various conditions of the object can be recognized precisely.

To evaluate the excellent performance of the inspection device of this invention, an experiment was actually conducted under the same conditions using the same inspection coil unit and sample specimens of the weld nuggets as used in the former embodiment. In the experiment, the phase change of the frequency fs and the amplitude strength of the induction current were measured while continuously changing the frequency of the alternating current Ir. The results of the experiment are shown in Table 1 below, and depicted in FIG. 14.

TABLE 1

| | Amplitude and Phase of Frequency of Applied and Induction Currents | | | |
|---|---|---|---|---|
| Frequency | Nondefective specimen (GD) | | Defective Specimen (NG) | |
| (kHz) | Amplitude | Phase | Amplitude | Phase |
| 8 | 0.74 (V) | 0 (*) | 0.65 (V) | 170 (*) |
| 10 | 0.97 | 0 | 0.87 | 50 |
| 15 | 1.35 | 0 | 1.26 | −15 |

TABLE 1-continued

| | Amplitude and Phase of Frequency of Applied and Induction Currents | | | |
|---|---|---|---|---|
| Frequency | Nondefective specimen (GD) | | Defective Specimen (NG) | |
| (kHz) | Amplitude | Phase | Amplitude | Phase |
| 20 | 1.75 | 0 | 1.62 | −15 |
| 25 | 2.12 | 0 | 2.00 | −20 |
| 30 | 2.50 | 0 | 2.39 | −20 |
| 35 | 2.90 | 0 | 2.80 | −21 |
| 40 | 3.29 | 0 | 3.25 | −22 |
| 45 | 3.72 | 0 | 3.59 | −23 |
| 50 | 4.20 | 0 | 4.20 | −23 |

Figure 14:
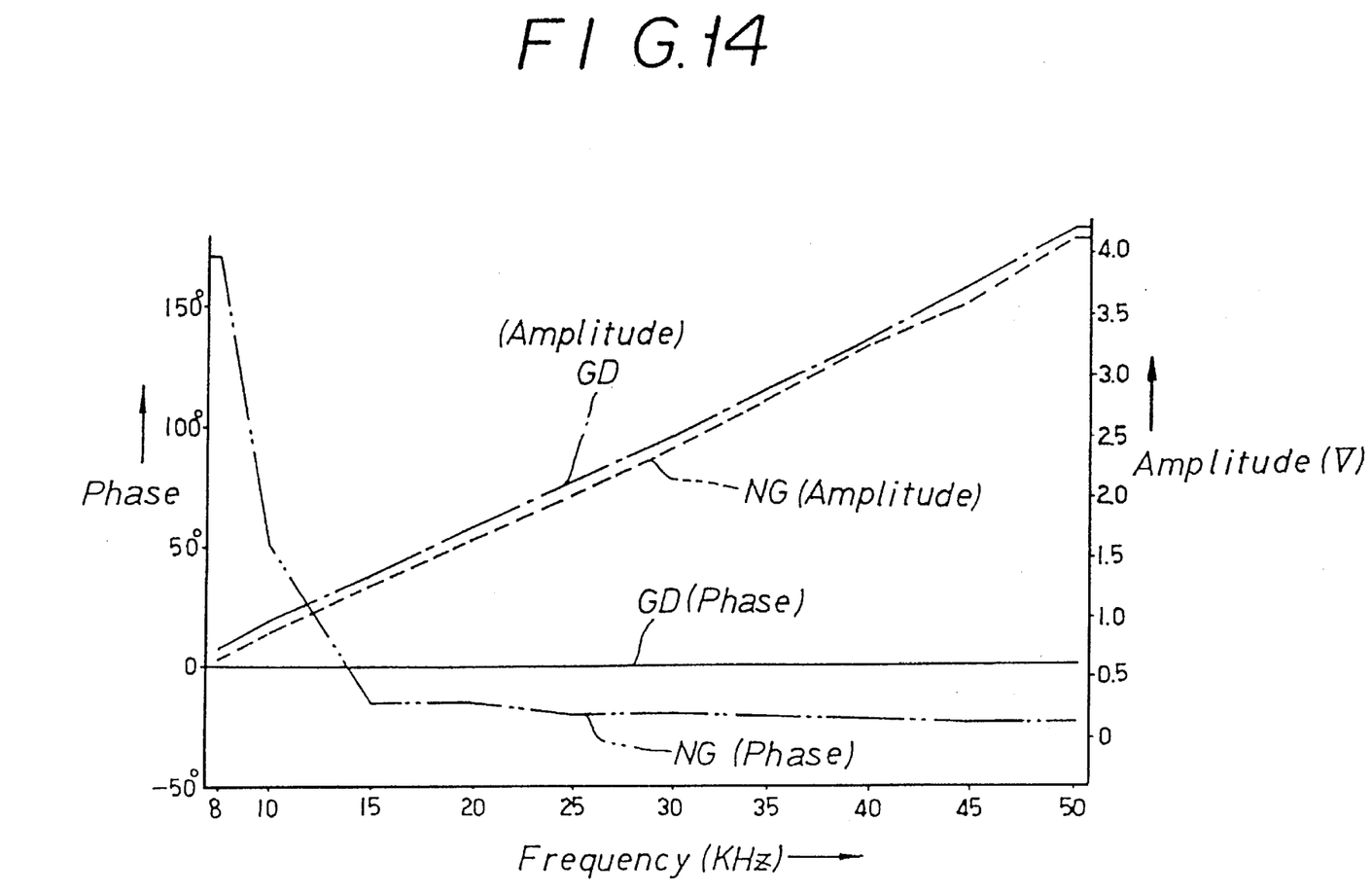
FIG. 14 is a frequency-phase characteristic diagram of another embodiment of this invention.

In FIG. 14, the frequency phases of the electromotive induction current are depicted at intervals of 5 kHz. In the experiment, the frequency phases of the induction current obtained when measuring the nondefective object (GD) were subject to zero adjustment every 5 kHz to facilitate understanding of the change of the frequency phase. As Is evident from the characteristic graph of FIG. 14, the frequency phase and amplitude (voltage) of the induction current obtained by measuring the defective object (NG) are distinctively different from those obtained by the nondefective object (GD). Also, the change patterns of the frequency phases of the induction currents obtained by measuring various defective objects are distinctively different according to the conditions of the defects in the objects.

Thus, by analyzing the changes of the frequency phase and amplitude of the induction current derived from the induction coil, not merely the material, size, physical properties and structure of the object but also the conditions of the defects in the object can be measured precisely.

As described above, the inspection device according to this invention utilizes electromagnetic induction which distinctively changes according to a given object placed in an electromagnetic field, thereby not only detecting the existence of the object but also measuring various conditions of the object and the defects in the object with a notably high accuracy. Since the amplitude and/or frequency phase of the induction current derived from the induction coil are analyzed, even minute change of the object to be measured can be reliably recognized as large differences in amplitude and frequency phase between the object and a reference body. The inspection coil unit used in this invention which includes the united primary exciting coil and secondary induction coil can detect the change in the electromagnetic field generated by the exciting coil with a high efficiency. Therefore, sensitivity and resolution of discriminating the conditions of the object can be remarkably improved, and a handy and portable inspection device of high performance can be accomplished.

It is to be understood that the invention is not limited in its application to the details of construction and arrangement of parts illustrated in the accompanying drawings, since the invention is capable of other embodiments and of being practiced or carried out in various ways. Also it is to be understood that the phraselogy or terminology employed herein is for the purpose of description and not of limitation.

What is claimed is:

1. An electromagnetic induction-type inspection device for discriminating defects of an object to be inspected, comprising:

a power source unit for issuing an alternating current and capable of continuously changing a frequency of the alternating current, an inspection coil unit including an exciting coil for generating an electromagnetic field upon application of the alternating current from said power source unit, and an induction coil for inducing an electromotive induction current in the electromagnetic field generated by said exciting coil, said exciting coil being applied with the alternating current from said power source unit while continuously changing the frequency of the alternating current, said electromotive induction current undergoing a change in amplitude and phase with the frequency of the alternating current applied to said exciting coil and in accordance with a configuration of a defect contained in an object placed in the electromagnetic field generated by said exciting coil, a measuring unit for measuring the electromotive induction current derived from said induction coil, said electromotive induction current being obtained as a reference induction value by placing a reference body in the electromagnetic field generated by said exciting coil, and said electromotive induction current being obtained as a measured induction value by placing the object to be inspected in the electromagnetic field, and means for discriminating a configuration of the defect of the object to be inspected by comparing said measured and reference induction values changing in amplitude and phase with the frequency of the alternating current applied to said exciting coil;

wherein said induction coil is wound closely around at least one part of said exciting coil while being electrically separated from said exciting coil so as to allow the magnetic field generated by said exciting coil to pass coaxially through said induction coil.

2. The inspection device according to claim 1 wherein said measuring unit detects an amplitude of the electromotive induction current derived from said induction coil to obtain the reference and measured induction values.

3. The inspection device according to claim 2 wherein the change of the amplitude of the electromotive induction current derived from said induction coil is represented as an induction characteristic pattern of the amplitude and compared with a predetermined reference induction characteristic pattern obtained from a change in the amplitude of the reference value, to thereby discriminate a defect of the object placed in the electromagnetic field.

4. The inspection device according to claim 1 wherein said measuring unit detects a phase of the electromotive induction current derived from said induction coil.

5. The inspection device according to claim 4 wherein the change of the phase of the electromotive induction current derived from said induction coil is represented as an induction characteristic pattern of the phase and compared with a predetermined reference induction characteristic pattern obtained from a change in the phase of the reference induction value, to thereby discriminate a defect of the object placed in the electromagnetic field.

6. The inspection device according to claim 1 wherein said measuring unit includes a comparator for comparing the change of the measured induction value with a change of the reference induction value to obtain a difference between the change of the measured induction value and the reference induction value, and an analyzer for discriminating a defect of the object to be inspected according to the difference issued from said comparator.

7. An inspection method for inspecting an object to discriminate a configuration of a defect of the object by use of an inspection coil unit including an exciting coil for generating an electromagnetic field upon application of alternating current, and an induction coil for inducing an electromotive induction current in the electromagnetic field generated by said exciting coil, wherein said induction coil is wound closely around at least one part of said exciting coil while being electrically separated from said exciting coil so as to allow the magnetic field generated by said exciting coil to pass coaxially through said induction coil, said exciting coil being applied with the alternating current from said power source unit while continuously changing a frequency of the alternating current, which comprises:

predetermining a reference induction value from the electromotive induction current continuously outputted from said induction coil when placing a reference body in the electromagnetic field generated by said exciting coil while continuously changing the frequency of the alternating current applied to said exciting coil, said reference induction value undergoing a change in amplitude and phase in accordance with the frequency of the applied alternating current, measuring a measured induction value from the electromotive induction current continuously outputted from said induction coil when placing the object to be inspected in the electromagnetic field generated by said exciting coil while continuously changing the frequency of the alternating current applied to said exciting coil, said measured induction value undergoing a change in amplitude and phase in accordance with the frequency of the applied alternating current, comparing said measured and reference induction values changing in amplitude and phase with the frequency of the alternating current applied to said exciting coil with each other, and discriminating the configuration of the defect of said object to be inspected in accordance with the comparison of the change in at least one of the amplitude and phase of said measured induction value.

8. The inspection method according to claim 7 wherein measured and reference induction change patterns are formed denoting a change in amplitude of the measured induction value and the reference induction value, respectively.

9. The inspection method according to claim 7 wherein measured and reference induction change patterns are formed denoting a change in phase of the measured induction value and the reference induction value, respectively.

10. The inspection method according to claim 7 wherein measured and reference induction change patterns are formed denoting changes in amplitude and phase of the measured induction value and the reference induction value, respectively.

11. The inspection method according to claim 7 wherein the electromotive current is detected by said induction coil which is wound around at least one part of said exciting coil while being electrically separated from said exciting coil so as to allow the magnetic field generated by exciting coil to pass coaxially through said induction coil.

* * * * *